(12) United States Patent
Stewart et al.

(10) Patent No.: US 11,865,519 B2
(45) Date of Patent: Jan. 9, 2024

(54) NOBLE METAL-PROMOTED IN2O3 CATALYST FOR THE HYDROGENATION OF CO2 TO METHANOL

(71) Applicants: TOTAL SE, Courbevoie (FR); ETH ZURICH, Zurich (CH)

(72) Inventors: Joseph Stewart, Uccle (BE); Daniel Curulla-Ferre, Uccle (BE); Javier Perez-Ramirez, Zürich (CH); Cecilia Mondelli, Zürich (CH); Matthias Frei, Zürich (CH)

(73) Assignees: TOTAL SE, Courbevoie (FR); ETH ZURICH, Zurich (CH)

( * ) Notice: Subject to any disclaimer, the term of this patent is extended or adjusted under 35 U.S.C. 154(b) by 269 days.

(21) Appl. No.: 17/273,108

(22) PCT Filed: Sep. 5, 2019

(86) PCT No.: PCT/EP2019/073662
§ 371 (c)(1),
(2) Date: Mar. 3, 2021

(87) PCT Pub. No.: WO2020/049082
PCT Pub. Date: Mar. 12, 2020

(65) Prior Publication Data
US 2021/0354114 A1    Nov. 18, 2021

(30) Foreign Application Priority Data

Sep. 6, 2018 (EP) ..................... 18306174
Sep. 6, 2018 (EP) ..................... 18306175

(51) Int. Cl.
*B01J 23/44* (2006.01)
*B01J 23/62* (2006.01)
*B01J 6/00* (2006.01)
*B01J 23/42* (2006.01)
*B01J 35/02* (2006.01)
*B01J 37/03* (2006.01)
*C07C 1/04* (2006.01)
*B01J 21/06* (2006.01)
*B01J 23/08* (2006.01)
*B01J 35/00* (2006.01)
*B01J 35/10* (2006.01)
*B01J 37/02* (2006.01)
*C07C 29/157* (2006.01)

(52) U.S. Cl.
CPC ............. *B01J 23/62* (2013.01); *B01J 6/001* (2013.01); *B01J 21/066* (2013.01); *B01J 23/08* (2013.01); *B01J 23/42* (2013.01); *B01J 23/44* (2013.01); *B01J 35/006* (2013.01); *B01J 35/023* (2013.01); *B01J 35/1014* (2013.01); *B01J 35/1019* (2013.01); *B01J 37/0201* (2013.01); *B01J 37/031* (2013.01); *C07C 1/043* (2013.01); *C07C 1/046* (2013.01); *C07C 29/157* (2013.01)

(58) Field of Classification Search
CPC ... B01J 23/62; B01J 23/08; B01J 23/42; B01J 23/44; B01J 35/023; B01J 35/1014; B01J 35/1019; B01J 37/031; B01J 37/0201; C01C 1/043; C01C 1/046; C07C 29/157
See application file for complete search history.

(56) References Cited

U.S. PATENT DOCUMENTS 7,279,138 B2    10/2007    Pagani et al.

FOREIGN PATENT DOCUMENTS

| CN | 106390978 A | | 2/2017 |
| EP | 2257366 B1 | | 7/2011 |
| JP | S5997048 | * | 6/1984 |
| JP | S5997048 A | | 6/1984 |
| WO | 2017/118572 A1 | | 7/2017 |
| WO | 2019053452 A1 | | 3/2019 |
| WO | WO-2019053452 A1 | * | 3/2019 |

OTHER PUBLICATIONS

Song et al., Catal. Lett., (2015), v.145, p. 1272-1280.*
Rui et al., Applied catalysis B: Environmental, (2017), v.218, p. 488-497.*
International Search Report issued in Application No. PCT/EP2019/073662, dated Dec. 13, 2019; 4 pages.
Felix Studt et al. "Discovery of a Ni—Ga Catalyst for Carbon Dioxide Reduction to Methanol", Nature Chemistry, vol. 6, Apr. 2014 (320-324).
Jijie Wang et al. "A Highly Selective and Stable ZnO—ZrO2 Solid Solution Catalyst for CO2 Hydrogenation to Methanol", Science Advances, 2017; vol. 3: e1701290; 10 pages.
Tadahiro Fujitani et al. "Development of an Active Ga2O3 Supported Palladium Catalyst for the Synthesis of Methanol from Carbon Dioxide and Hydrogen", Applied Catalysis A: General, vol. 125 (1995) L199-L202.
Jingyun Ye et al. "Methanol Synthesis from CO2 Hydrogenation over a Pd4/In2O3 Model Catalyst: a Combined DFT and Kinetic Study", Journal of Catalysis, vol. 317 (2014) pp. 44-53.
Yong Men et al. "Methanol Stream Reforming Over Bimetallic Pd—In/Al2O3 Catalysts in a Microstructured Reactor" Applied Catalysis A: General, vol. 380 (2010) pp. 15-20.
Harald Lorenz et al. "Pd—In2O3 interaction due to Reduction in Hydrogen: Consequences for Methanol Stream Reforming", Applied Catalysis A: General, vol. 374 (2010) pp. 180-188.

(Continued)

*Primary Examiner* — Yong L Chu
(74) *Attorney, Agent, or Firm* — Ewing & Jones, PLLC

(57) ABSTRACT

Method to prepare a catalyst for use in a process for the synthesis of methanol, comprising indium oxide in the form of $In_2O_3$, and at least one additional metal selected from a noble metal; and in that the average particle size of said noble metal phase is, preferably at least 0.05 nm, and less than 5 nm as determined by STEM-EDX, characterized in that the catalyst is prepared by co-precipitation of a saline solution at a pH above 8.5 comprising an indium salt and a salt of the at least one additional metal selected from a noble metal and optionally further comprising a salt of the at least one alkaline earth metal.

11 Claims, 4 Drawing Sheets

(56) References Cited

OTHER PUBLICATIONS

Rui Ning et al. "$CO_2$ hydrogenation to methanol over Pd/$In_2O_3$: effects of Pd/$In_2O_3$: effects of Pd and oxygen vacancy", Applied catalysis B: environmental, vol. 218, Jun. 23, 2017 pp. 488-497.

Xiao Jiang, et al. "Bimetallic Pd—Cu Catalysts for Selective $CO_2$ Hydrogenation to Methanol", Applied Catalysis B: Environmental, vol. 170-171 (2015) pp. 173-185.

Antje Ota et al. "Comparative Study of Hydrotalcite-Derived Supported $Pd_2Ga$ and PdZn Intermetallic Nanoparticles as Methanol Synthesis and Methanol Steam Reforming Catalysts", Journal of catalysis, vol. 293 (2012) pp. 27-38.

Matthias Neumann et al. "Controlled Synthesis and Catalytic Properties of Supported In-Pd Intermetallic Compound", Journal of Catalysis, vol. 340 (2016) pp. 49-59.

Jingyun Ye et al. "Effect of PdIn Bimetallic Particle Formation on $CO_2$ Reduction over the Pd—In/$SiO_2$ Catalyst", Chemical Engineering Science, vol. 135 (2015) pp. 193-201.

Christoph Rameshan, et al., "Impregnated and Co-precipitated Pd—$Ga_2O_3$, Pd—$In_2O_3$ and Pd—$Ga_2O_3$—$In_2O_3$ Catalysts: Influence of the Microstructure on the $CO_2$ Selectivity in Methanol Steam Reforming", Catalysis Letters, vol. 148, No. 10, 2018, pp. 3062-3071.

Di Liu, et al. "Highly Active and Durable Pt/$In_2O_3$/$Al_2O_3$ Catalysts in Methanol Steam Reforming" International Journal of Hydrogen Energy, vol. 41, 2016, pp. 21990-21999.

Roland L. Barbosa et al. "Methanol Steam Reforming Over Indium-Promoted Pt/$Al_2O_3$ Catalyst : Nature of the Active Surface" Journal of Physical Chemistry C, vol. 117, 2013, pp. 6143-6150.

M.S. Frei et al., "Mechanism and microkinetics of methanol synthesis via $CO_2$ hydrogenation on indium oxide", J. Catal., 2018, vol. 361, pp. 313-321.

* cited by examiner

NOBLE METAL-PROMOTED IN2O3 CATALYST FOR THE HYDROGENATION OF CO2 TO METHANOL

CROSS-REFERENCE TO RELATED APPLICATIONS

This application claims the benefit of PCT/EP2019/073662 filed Sep. 5, 2019, which claims priority from EP 18306174.6 filed Sep. 6, 2018 and EP 18306175.3 filed Sep. 6, 2018, which are incorporated herein by reference in their entireties for all purposes.

FIELD OF THE INVENTION

The invention relates to a process for the synthesis of methanol from $CO_2$-containing stream feeds. It also relates to the catalyst used in such a process.

BACKGROUND OF THE INVENTION

As part of the drive to tackle the growing global climate problem, it is attempted to reduce $CO_2$ levels. In order to reach the targets set out by the COP21 agreement, $CO_2$ emissions must be reduced by 50-85% by 2050. There are two main approaches, carbon capture and storage (CCS) and carbon capture and utilization (CCU), in which $CO_2$ is trapped, released in a controlled manner, and converted into products or intermediate building blocks.

Currently, there is much work on carbon capture technology and much debate on which technology will be the one to take off to be both financially and environmentally viable. No matter which technology emerges as the standout carbon capture process, the need to use this captured $CO_2$ as a lucrative Ci source is undeniable. $CO_2$ utilization is a subject that has attracted a lot of attention over the past decade and beyond. Advances are not restricted to fine chemicals but they also apply to the incorporation of $CO_2$ into polymer structures, either as a monomer or as a precursor to a monomer.

Of particular interest is the synthesis of methanol. This chemical is a convenient liquid fuel and a raw material for synthetic hydrocarbons, which offers an alternative to depleting fossil fuels. Although it is currently industrialized by the conversion of $H_2$ and CO, methanol can be synthesized via the hydrogenation of $CO_2$. The conversion of $CO_2$ into methanol would allow a promising cycle, in which $CO_2$ can be converted to an energy storage compound, methanol, which can then be used giving $CO_2$ back, which can in turn be recaptured. Studies in this area are rapidly increasing, with the desire to find a stable, active, and selective catalyst for $CO_2$ conversion into methanol.

$$CO + 2H_2 \rightarrow CH_3OH$$

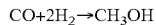

$$CO_2 + 3H_2 \rightarrow CH_3OH + H_2O$$

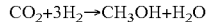

Several catalysts have been proposed and studied to perform methanol synthesis from $CO_2$. For example, Felix Studt et al. in "*Discovery of a Ni—Ga Catalyst for Carbon Dioxide Reduction to Methanol*", Nature Chemistry, Vol. 6, April 2014 (320-324), describes the use of a Ni—Ga catalyst that reduces $CO_2$ to methanol at ambient pressure.

More recently, WO2017/118572 describes an indium-based catalytic system and a process for methanol synthesis from a $CO_2$-containing syngas. The catalyst introduced is an indium oxide supported on zirconia system that exhibits 100% selectivity towards methanol, good stability up to 1000 h in the presence of $CO_2$ as the sole carbon source and high activity. The stability of the catalyst was particularly interesting since when it was benchmarked against a conventional Cu-based methanol synthesis catalyst, the Cu-based catalyst showed significant loss of activity (loss of 44% activity within 100 h) due to the co-production of water when converting $CO_2$.

The effect of zirconium dioxide as a catalyst was also studied in "*A Highly Selective and Stable ZnO—ZrO₂ Solid Solution Catalyst for CO₂ Hydrogenation to Methanol*", Jijie Wang et al. Science Advances, 2017; 3: e1701290. The methanol selectivity achieved was of up to 86-91% with a $CO_2$ single-pass conversion of more than 10% under the reported reaction conditions. Zr and Zn showed a synergetic effect and the ZnO—ZrO₂ catalyst demonstrated a high stability for at least 500 h on stream. In addition, it did not deactivate in the presence of 50 ppm of $SO_2$ or $H_2S$.

CN106390978 reports catalysts for synthesis of methanol through carbon dioxide hydrogenation. The catalysts are produced by co-precipitation of two metal oxides. In particular, the ZnO—ZrO₂ catalyst was found to have a methanol selectivity of 80%.

Palladium-based catalysts have also been considered for a long time. In 1995, Tadahiro Fujitani et al. in "*Development of an Active Ga₂O₃ Supported Palladium Catalyst for the Synthesis of Methanol from Carbon Dioxide and Hydrogen*", Applied Catalysis A: General 125 (1995) L199-L200, already came to the conclusion that there was a significant effect of the support on the catalytic activity of palladium-based catalysts for methanol synthesis from carbon dioxide and hydrogen.

Jingyun Ye et al. in "*Methanol Synthesis from CO₂ Hydrogenation over a Pd₄/In₂O₃ Model Catalyst: a Combined DFT and Kinetic Study*", Journal of Catalysis 317 (2014) 44-53, have examined three possible routes in the reaction network to produce methanol and water. The density functional theory (DFT) results showed that the HCOO route competes with the reverse water-gas shift (RWGS) route.

Yong Men et al. in "*Methanol Stream Reforming Over Bimetallic Pd—In/Al₂O₃ Catalysts in a Microstructured Reactor*"; Applied Catalysis A: General 380 (2010) 15-20, describe the use of bimetallic PdIn catalysts. The catalytic activity and $CO_2$ selectivity were found to be markedly dependent on the Pd:In ratio as well as on the metal loading. The high $CO_2$ selectivity of Pd—In/Al₂O₃ catalysts has been ascribed to the Pd—In alloy formation, whereas the metallic Pd without contact with indium is responsible for CO selectivity.

The Pd—In₂O₃ interaction and their effect on the catalytic activity were further studied. Harald Lorenz et al. in "*Pd—In₂O₃ interaction due to Reduction in Hydrogen: Consequences for Methanol Stream Reforming*", Applied Catalysis A: General 374 (2010) 180-188, showed that oxidative treatments of the bimetallic PdIn catalysts led to the decomposition of PdIn and the formation of an In₂O₃ shell covering the Pd particles.

More recently, Pd—In catalysts wherein the formation of Pd—In bimetallic species was avoided have also been produced and tested. "*CO₂ Hydrogenation to Methanol over Pd/In₂O₃; effects of Pd and Oxygen Vacancy*"; Ning Riu et al. Applied Catalysis B: Environmental, 218 (2017) 488-497 reports the results of these experiments. The formation of Pd—In bimetallic species was found to reduce the methanol yield. Thus, a new catalyst consists of $In_2O_3$ highly-dispersed Pd-nanoparticles predominately exposing the (111) faces with an average particle size of 3.6 nm. The catalysts tested showed superior performances for $CO_2$ hydrogenation to methanol with a $CO_2$ conversion over 20% and methanol selectivity over 70%, corresponding to a space-time yield (STY) up to 0.89 $g_{MeOH}$ $h^{-1}$ $g_{CAT}^{-1}$ at 300° C. and 5 MPa.

Pd—Cu catalysts were also studied. Xiao Jiang et al. in "*Bimetallic Pd—Cu Catalysts for Selective $CO_2$ Hydrogenation to Methanol*", Applied Catalysis B: Environmental 170-171 (2015) 173-185, reported a strong synergetic effect on promoting methanol formation over amorphous silica supported Pd—Cu bimetallic catalysts when the Pd/(Pd+Cu) atomic ratios lied in the range of 0.25 to 0.34.

Antje Ota et al. in "*Comparative Study of Hydrotalcite-Derived Supported $Pd_2Ga$ and PdZn intermetallic nanoparticles as methanol synthesis and methanol Steam Reforming Catalysts*" Journal of catalysis 293 (2012) 27-38, described an improved selectivity to CO and to methanol for catalysts comprising Zn or Ga.

Matthias Neumann et al. in "*Controlled Synthesis and Catalytic Properties of Supported In—Pd Intermetallic Compound*" Journal of Catalysis 340 (2016) 49-59, described the formation of different intermetallic In—Pd by reduction of $PdO/In_2O_3$ with hydrogen. The materials produced exhibited catalytic activity for methanol steam reforming and high $CO_2$ selectivities of up to 98%. Long term measurements proved the superior stability of the In—$Pd/In_2O_3$ materials in comparison to Cu-based systems over 100 h on stream with high selectivity.

Rui Ning et al. in "*CO2 hydrogenation to methanol over $Pd/In2O3$: effects of $Pd/In2O3$: effects of Pd and oxygen vacancy*", Applied catalysis B: environmental Vol 218, 23 Jun. 2017 pages 488-497 described the conversion of $CO_2$ into methanol on a catalyst prepared via deposition of Pd peptide composite on $In_2O_3$.

Christoph Rameshan et al. in "*Impregnated and co-precipitated Pd—Ga2O3, Pd—In2O3 and Pd—Ga2O3-In2O3 catalysts: Influence of the microstructure on the CO2 selectivity in methanol steam reforming*", Catalysis Letters, Vol 148, No 10, October 2018, pages 3062-3071 described the steam reforming of methanol on a Pd—In2O3 catalyst prepared via co precipitation at a pH of 8.

Di Liu Ed-Kurt Erol et al. "*Highly active and durable Pt/In2O3/Al2O3catalysts in methanol steam reforming*" International Journal of Hydrogen Energy, Vol 41, No 47-21, December 2016, pages 21990-21999 described methanol steam reforming on a Pt/In2O3/Al2O3 catalyst prepared via incipient-wetness impregnation.

Roland L. Barbosa et al. "*Methanol steam reforming over Indium-promoted Pt/Al2O3 catalyst: Nature of the active surface*" Journal of Physical Chemistry C, Vol. 117, No 12, 28 Mar. 2013 described the methanol steam reforming performed over Al2O3 wash coated onto microchannels stainless steel sheets impregnated simultaneously with Pt and In.

Jingyun Ye et al. in "*Effect of PdIn Bimetallic Particle Formation on $CO_2$ Reduction over the Pd—$In/SiO_2$ Catalyst*" Chemical Engineering Science 135 (2015) 193-201, discovers that Pd—$In/SiO_2$ catalysts showed 100% selectivity toward CO and no detectacle $CH_4$ formation. This selectivity to CO was found to be a result of the formation of bimetallic Pd—In species.

Thus, there is still a need to find a new catalyst and a new process for the conversion of $CO_2$ to methanol.

SUMMARY OF THE INVENTION

The present invention provides the solution to one or more of the aforementioned needs. It is an object of the invention to provide a new process and a method of preparation of a catalyst for methanol synthesis from $CO_2$. Another object of the invention is to provide a new process and a new method of preparation of a catalyst allowing improvements in $CO_2$ conversion into methanol. Another object of the invention is to provide a method of preparation of a catalyst and a process for methanol synthesis showing improvements in $CO_2$ conversion to methanol, together with high space-time yield and high selectivity to methanol. Another object of the invention is to provide a method of preparation of a catalyst and a process for methanol synthesis showing high stability of the catalyst.

According to a first aspect, the invention provides a method of preparation of a catalyst for use in a process for the synthesis of methanol, wherein the catalyst comprises indium oxide in the form of $In_2O_3$, and at least one additional metal selected from a noble metal, and further wherein the average particle size of the one or more noble metal phase is, preferably at least 0.05 nm, less than 5 nm as determined by scanning transmission electron microscopy coupled to energy-dispersive X-ray spectroscopy (STEM-EDX) remarkable in that the catalyst is prepared by co-precipitation of a saline solution at a pH above 8.5 comprising an indium salt and a salt of the at least one additional metal selected from a noble metal and optionally further comprising a salt of the at least one alkaline earth metal.

Indeed, it has been found by the inventors that noble-metal promoted indium catalysts produced by co-precipitation enhanced productivity while guaranteeing very high stability under the defined reaction conditions in a process of hydrogenation of $CO_2$ to methanol, as opposed to the catalysts produced by impregnation. Indeed, as demonstrated in the examples, the productivity (expressed as space-time yield) was increased by a factor 6 compared to the bulk oxide. The co-precipitated materials also were stable up to 500 h on stream, while the impregnated analogues displayed activity loss within the first 24 h on stream. Also, it has been found that the average particle size of the noble metal phase is relevant regarding its sustained productivity.

With preference, the method of preparation of the catalyst is further remarkable in that the catalyst exhibits the additional noble metal in oxidized form and/or in that the catalyst further comprises at least one alkaline earth metal being preferably incorporated simultaneously with said indium salt and a said salt of the at least one additional metal selected from a noble metal at the co-precipitation stage.

Indeed, it has been found by the inventors that the catalyst exhibits the presence of the additional noble metal is in its oxidized form after synthesis and in reduced form under reaction conditions as determined by XPS. With preference, the noble metal is palladium and the metal is in its 2+oxidation state.

In an embodiment, the $In_2O_3$ is present in the form of particles having an average crystal size of less than 20 nm as determined by XRD; preferably, the average crystal size of $In_2O_3$ is less than 15 nm; more preferably less than 12 nm; and even more preferably, less than 10 nm.

With preference, one or more of the following features can be used to better define the catalyst obtained by the inventive method:
said co-precipitation is performed at a pH above 9; and at a temperature of at least 293 K (19.85° C.)
said method of preparation is further remarkable in that the catalyst is a calcined catalyst, and in that the method comprises a step of calcination of the catalyst performed at a temperature of at least 473 K (199.85° C.), with preference of at least 573 K (299.85° C.).

The catalyst obtained by said method contains at least one additional metal being a noble metal selected from ruthenium (Ru), rhodium (Rh), palladium (Pd), silver (Ag), osmium (Os), platinum (Pt), copper (Cu), gold (Au), iridium (Ir), and any combination thereof; preferably a noble metal selected from ruthenium (Ru), rhodium (Rh), palladium (Pd), silver (Ag), platinum (Pt), copper (Cu), and any combination thereof; more preferably, a noble metal selected from ruthenium (Ru), rhodium (Rh), palladium (Pd), silver (Ag), platinum (Pt), and any combination thereof; even more preferably, a noble metal selected from palladium (Pd) and/or platinum (Pt), and most preferably the noble metal is palladium (Pd).

The catalyst obtained is further calcined and shows a crystalline structure as determined by XRD.

The catalyst obtained exhibits an initial signal in temperature programmed reduction with $H_2$ at 5.0 MPa of less than 300 K.

The catalyst obtained is a calcined catalyst and it comprises from 0.01 to 10 wt. % of the additional metal based on the total weight of the calcined catalyst, preferably from 0.1 to 7.0 wt. %, more preferably from 0.3 to 5.0 wt. %; even more preferably from 0.5 to 2.0 wt. %; and most preferably from 0.6 to 1.0 wt %.

The average particle size of the noble metal phase on the obtained catalyst is less than 4 nm, with preference less than 2 nm as determined by STEM-EDX.

The catalyst is obtained a calcined catalyst and the indium oxide content in the form of $In_2O_3$ based on the calcined catalyst ranges from 50 to 99.9 wt. %, preferably from 93 to 99.5 wt. %.

According to a second aspect, the invention provides a process for methanol synthesis comprising the following steps:
  providing a feed stream comprising hydrogen and carbon oxides selected from carbon dioxide or a mixture of carbon dioxide and carbon monoxide, wherein carbon dioxide represents from 1 to 50 mol % of the total molar content of the feed stream, carbon monoxide is contained from 0 to 85 mol % of the total molar content, and $H_2$ is comprised from 5 to 99 mol % of the total molar content of the feed stream;
  providing a catalyst according to the first aspect and/or prepared according to the second aspect;
  putting said feed stream in contact with said catalyst at a reaction temperature of at least 373 K (99.85° C.) and under a pressure of at least 0.5 MPa; and
  recovering the methanol from the effluents by a separation process.

With preference, one or more of the following features can be used to better define the inventive process:
  The process is carried out in a gaseous phase.
  The reaction temperature is at least 463 K (189.85° C.), preferably at least 523 K (249.85° C.), more preferably at least 553 K (279.85° C.).
  The reaction temperature is at most 773 K (499.85° C.).
  The reaction pressure is at least 1 MPa, preferably at least 2 MPa, more preferably at least 3 MPa, even more preferably at least 4 MPa, most preferably at least 5 MPa.
  The reaction pressure is at most 50 MPa, preferably at most 25 MPa, more preferably at most 10 MPa.
  The feed stream comprises at least 3 mol % of $CO_2$ based on the total molar content of the feed stream, preferably at least 5 mol %, more preferably at least 10 mol %, even more preferably at least 20 mol %. The feed comprises at most 40 mol % of $CO_2$ based on the total molar content of the feed stream, preferably at most 35 mol %, more preferably at most 30 mol %.
  The feed stream comprises preferably at least 1 mol % of CO based on the total molar content of the feed stream, preferably at least 2 mol %, more preferably at least 10 mol %.
  The feed stream comprises at most 75 mol % of CO based on the total molar content of the feed stream, preferably at most 65 mol %, more preferably at most 50 mol %.
  The feed stream comprises at least 10 mol % of $H_2$ based on the total molar content of the feed stream, preferably at least 20 mol %, more preferably at least 30 mol %.
  The feed stream comprises at most 90 mol % of $H_2$ based on the total molar content of the feed stream, preferably at most 80 mol %, more preferably at most 70 mol %, even more preferably at most 60 mol %.
  The feed stream comprises a mixture of carbon dioxide and carbon monoxide and the feed stream contains at most 30 mol % of $CO_2$ based on the total molar content of the carbon oxide, or the feed stream comprises a mixture of carbon dioxide and carbon monoxide and the feed stream contains more than 30 mol % of $CO_2$ based on the total molar content of the carbon oxide.
  The molar ratio of hydrogen to carbon dioxide ($H_2$:$CO_2$) in the feed stream is at least 1:1, preferably it is at least 3:1, and more preferably it is at least 4:1.
  The feed stream is put in contact with the catalyst at a weight hourly space velocity (WHSV) ranging from 3,000 to 60,000 $cm^3_{STP}$ $g_{cat}$ $h^{-1}$; preferably of at least 16,000 $cm^3_{STP}$ $g_{cat}$ $h^{-1}$, more preferably of at least 24,000 $cm^3_{STP}$ $g_{cat}$ $h^{-1}$, and even more preferably of at least 48,000 $cm^3_{STP}$ $g_{cat}$ $h^{-1}$.
  The process is carried out during more than 100 h, preferably more than 1,000 h, more preferably more than 10,000 h, even more preferably more than 100,000 without replacement or reactivation of the co-precipitated catalyst.

In an embodiment, prior to reaction the catalyst is activated in situ by raising the temperature to at least 553 K (279.85° C.) in a flow of a gas feed stream for activation selected from inert gases, hydrogen, carbon monoxide, carbon dioxide or mixture thereof, preferably the gas feed stream for activation is or comprises an inert gas, more preferably the gas feed stream for activation is or comprises nitrogen According to a third aspect, the invention provides the use of a catalyst obtained according to the first aspect in a process of hydrogenation of $CO_2$ to methanol.

DETAILED DESCRIPTION OF THE INVENTION

Figure 1:
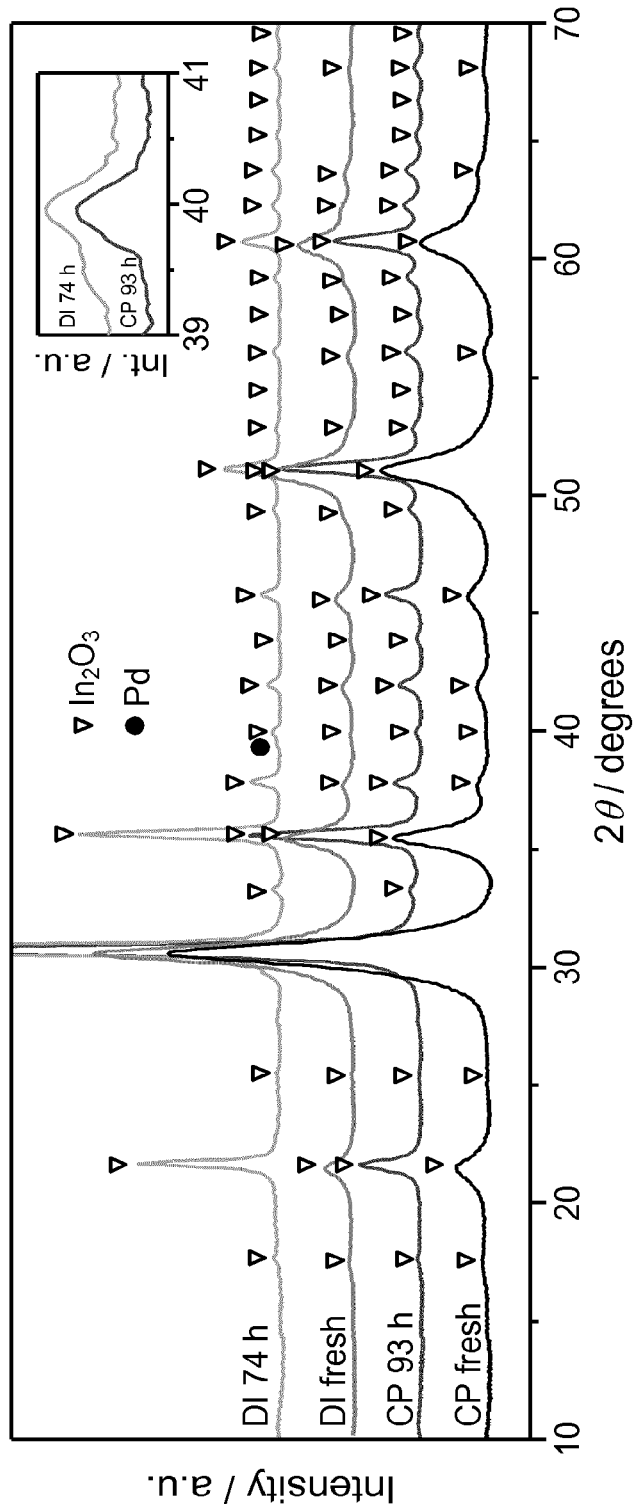
FIG. 1 shows the X-ray diffraction (XRD) patterns of Pd—$In_2O_3$ samples prepared by dry impregnation and co-precipitation in fresh form and after use in the reaction.

As used herein the generic term "catalyst" refers to both a "bulk" and a "supported catalyst". A bulk catalyst is a catalyst containing the additional metal (i.e., the alkali and/or the noble metal) without its support (in this case the indium oxide). A co-precipitated catalyst is a catalyst wherein the active phase is intimately mixed with the support, in contrast with spray deposition techniques and impregnation techniques wherein the active phase is deposited on the support. Although impregnation is one of the easiest methods for producing a catalyst, it has been found that the homogeneity of product, especially for high metal loading, and the reproducibility of this process are better when a co-precipitation strategy is applied. The nature of the interaction of the material components is different between impregnated material and co-precipitated materials.

In methanol synthesis according to the invention, a feed gas composed of hydrogen gas and carbon oxides ($CO_2$ alone or a mixture of $CO_2$ and CO gases) are caused to interact on an indium oxide-based catalyst produced by co-precipitation with a noble metal.

The noble metals are metals resistant to corrosion and oxidation and are selected from ruthenium (Ru), rhodium (Rh), palladium (Pd), silver (Ag), osmium (Os), platinum (Pt), copper (Cu), gold (Au) and iridium (Ir). In a preferred embodiment of the invention, the catalyst is devoid of gold (Au).

The alkaline earth metals are selected from beryllium (Be), magnesium (Mg), calcium (Ca), strontium (Sr), barium (Ba), and radium (Ra).

Catalyst and Preparation of the Catalyst

The present invention contemplates the use of a catalyst in a process for the synthesis of methanol, wherein the catalyst comprises indium oxide in the form of $In_2O_3$, at least one additional noble metal selected from a noble metal and optionally at least one alkaline earth metal; further wherein the average particle size of the one or more noble metal phase is, preferably at least 0.05 nm, less than 5 nm as determined by STEM-EDX.

According to the invention, the fresh catalyst exhibits the additional noble metal in oxidized form after synthesis and in reduced form under reaction conditions as determined by XPS.

In a preferred embodiment, the catalyst comprises indium oxide in the form of $In_2O_3$, at least one additional noble metal selected from a noble metal, and optionally at least one alkaline earth metal; further wherein the average particle size of the one or more noble metal phase is less, preferably at least 0.05 nm, than 5 nm as determined by STEM-EDX; $In_2O_3$ is present in the form of particles having an average crystal size of less than 20 nm as determined by XRD.

In an embodiment, the $In_2O_3$ is present in the form of particles having an average crystal size of less than 20 nm as determined by XRD; preferably, the average crystal size of $In_2O_3$ is less than 15 nm; more preferably less than 12 nm; and even more preferably, less than 10 nm.

The catalyst is a catalyst prepared by co-precipitation, an average particle size of less than 5 nm, preferably less than 2 nm, for both the noble-metal and the optional alkaline-earth metal after deactivation of the catalyst, allow to differentiate it from the catalysts wherein the noble metal is deposited on the support by impregnation or deposition techniques. Thus, is an embodiment, the noble metal average particle size after use of the catalyst is less, preferably at least 0.05 nm, than 5 nm as determined by STEM-EDX. To the contrary, when the catalyst is prepared by impregnation or deposition techniques the noble metal particle will agglomerate under reaction conditions, and therefore the noble metal average particle size will be larger after use than before use.

According to an embodiment, the catalyst exhibits an initial signal in temperature-programmed reduction with $H_2$ at 5.0 MPa of less than 300 K.

Based on the nature of the synthesis strategy as well as XRD, XPS, and STEM-EDX analyses, it is conceivable that the noble metal is homogeneously distributed (possibly even atomically) through the bulk of $In_2O_3$ for the material prepared by co-precipitation, whereas it is present in the form of highly dispersed clusters for materials prepared by impregnation or other deposition techniques. STEM-EDX analyses is preferred to determine the size of crystals and/or particles lower than 10 nm.

In a preferred embodiment, the average size of the noble metal phase is less, preferably at least 0.05 nm, than 5 nm as determined by STEM-EDX, preferably less than 4 nm, more preferably less than 2 nm.

In an embodiment, the at least one noble metal is selected from ruthenium (Ru), rhodium (Rh), palladium (Pd), silver (Ag), osmium (Os), platinum (Pt), copper (Cu), gold (Au), iridium (Ir), and any combination thereof; preferably a noble metal selected from ruthenium (Ru), rhodium (Rh), palladium (Pd), silver (Ag), platinum (Pt), copper (Cu), and any combination thereof; more preferably, a noble metal selected from ruthenium (Ru), rhodium (Rh), palladium (Pd), silver (Ag), platinum (Pt), and any combination thereof; even more preferably, a noble metal selected from palladium (Pd) and/or platinum (Pt), and most preferably the noble metal is palladium (Pd)

The catalyst is preferably a calcined catalyst. This feature can be evidenced by the loss of the indium hydroxide form and formation of the pattern attributed to an indium oxide form observed in the X-ray diffraction.

In an embodiment, the catalyst is a calcined catalyst and comprises from 0.01 to 10 wt. % of the at least one additional noble metal based on the total weight of the calcined catalyst.

With preference, the catalyst is a calcined catalyst and comprises at least 0.1 wt. % of the at least one additional noble metal based on the total weight of the calcined catalyst, preferably at least 0.3 wt. %, more preferably at least 0.5 wt. %, even more preferably at least 0.6 wt. %, and most preferably at least 0.7 wt. %.

With preference, the catalyst is a calcined catalyst and comprises at most 10.0 wt. % of the at least one additional noble metal based on the total weight of the calcined catalyst, preferably at most 7.0 wt. %, more preferably at most 5.0 wt. %, even more preferably at most 2.0 wt. %, and most preferably at most 1.0 wt. %.

When present, the at least one alkaline earth metal is selected from beryllium (Be), magnesium (Mg), calcium (Ca), strontium (Sr), barium (Ba), radium (Ra), and any combination thereof.

With preference, the catalyst is a calcined catalyst and comprises at least 0.1 wt. % of at least one alkaline earth metal based on the total weight of the calcined catalyst, preferably at least 0.3 wt. %, more preferably at least 0.5 wt. %, even more preferably at least 0.6 wt. %, and most preferably at least 0.7 wt. %.

With preference, the catalyst is a calcined catalyst and comprises at most 10.0 wt. % of at least one alkaline earth metal based on the total weight of the calcined catalyst, preferably at most 7.0 wt. %, more preferably at most 5.0 wt. %, even more preferably at most 2.0 wt. %, and most preferably at most 1.0 wt. %.

In an embodiment, the catalyst is a calcined catalyst and the indium oxide content in the form of $In_2O_3$ based on the calcined catalyst is ranging from 50 to 99.99 wt. %, preferably from 93 to 99.5 wt. %.

With preference, the catalyst is a calcined catalyst and comprises at least 60 wt. % of indium oxide based on the total weight of the calcined catalyst, preferably at least 70 wt. %, more preferably at least 80 wt. %, even more preferably at least 90 wt. %, and most preferably at least 95 wt. %.

With preference, the catalyst is a calcined catalyst and comprises at most 99 wt. % of indium oxide based on the total weight of the calcined catalyst, preferably at most 98.5 wt. %, more preferably at most 98 wt. %, and even more preferably at most 97.5 wt. %.

According to the invention, the catalyst is prepared by co-precipitation performed at a pH above 8.5 of a saline solution comprising an indium salt and a salt of the at least an additional metal selected from a noble metal and optionally further comprising a salt of the at least one alkaline earth metal.

With preference, the catalyst is prepared by co-precipitation of a saline solution comprising $In(NO_3)_3 \cdot xH_2O$ and a salt of the at least additional metal selected from a noble metal and optionally further comprising a salt of the at least one alkaline earth metal.

In a preferred embodiment the noble metal is palladium. With preference, the salt is $Pd(NO_3)_2$.

With preference, the co-precipitation is above 9; and at a temperature of at least 293 K (19.85° C.).

In a preferred embodiment, the catalyst is a calcined catalyst, and the method comprises a step of calcination of the catalyst performed after the co-precipitation step. The calcination is preferably performed at a temperature of at least 473 K, with preference of at least 573 K.

Hydrogenation of Carbon Dioxide to Methanol

In methanol synthesis according to the invention, a feed gas composed of hydrogen gas and carbon oxides ($CO_2$ alone or a mixture of $CO_2$ and CO gases) are caused to interact on an indium oxide-based catalyst.

The invention provides a process for methanol synthesis comprising the following steps:
providing a feed stream comprising hydrogen and carbon oxides selected from carbon dioxide or a mixture of carbon dioxide and carbon monoxide, wherein carbon dioxide represents from 1 to 50 mol % of the total molar content of the feed stream, carbon monoxide is contained from 0 to 85 mol % of the total molar content, and $H_2$ is comprised from 5 to 99 mol % of the total molar content of the feed stream;
providing a catalyst comprising indium oxide in the form of $In_2O_3$, and at least one additional metal selected from a noble metal; and in that the average particle size of the one or more noble metal phase is, preferably at least 0.05 nm, less than 5 nm as determined by STEM-EDX;
putting in contact said feed stream with said catalyst at a reaction temperature of at least 373 K (99.85° C.) and under a pressure of at least 0.5 MPa; and
recovering the methanol from the effluents by a separation process.

The process can be carried out in a gaseous phase or in a liquid phase. The solvent that can be used for the reaction in liquid phase includes hydrocarbons and other solvents which are preferably insoluble or only sparingly soluble in water. Preferably, the process is carried out in a gaseous phase.

Prior to reaction the catalyst is activated in situ by raising the temperature to at least 553 K (279.15° C.) in a flow of a gas feed stream for activation selected from inert gases, hydrogen, carbon monoxide, carbon dioxide, or a mixture thereof, preferably the gas feed stream for activation is or comprises an inert gas, more preferably the gas feed stream for activation is or comprises nitrogen.

The process is carried out in a reactor comprising:
lines to introduce a feed stream to the reactor and remove products from the reactor;
a device for heating the reactor;
a temperature sensor and controller for detecting and controlling the temperature of the reactor at a reaction temperature chosen between 373 K (99.85° C.) and 773 K (499.85° C.)
flow controllers to control the rate of the feed stream to the reactor; and
a pressure controller to control the reactor pressure in order to set it at a pressure of at least 0.5 MPa.

In accordance to the invention, the feed stream comprises hydrogen and carbon oxides selected from carbon dioxide ($CO_2$) or a mixture of carbon dioxide and carbon monoxide. However, in a preferred embodiment, the feed stream comprises hydrogen and carbon dioxide.

When the feed stream comprises hydrogen and a mixture of carbon dioxide and carbon monoxide, the feed stream can be CO-rich or $CO_2$-rich. In accordance to the invention, $CO_2$-rich feed stream contains more than 30 mol % of $CO_2$ based on the total molar content of the carbon oxide. In a preferred embodiment of the invention, the feed stream is $CO_2$-rich.

The feed stream comprises $CO_2$ and $H_2$, or $H_2$ and a mixture of $CO_2$ and CO, preferably the feed stream may also comprise a further gaseous component such as an inert gas. The inert gas is for example nitrogen.

In a preferred embodiment, the molar ratio of hydrogen to carbon dioxide in the feed stream is at least 1:1, preferably at least 3:1, more preferably at least 4:1, even more preferably at least 6:1; and/or the molar ratio of hydrogen to carbon dioxide in the feed stream is at most 12:1.

In a preferred embodiment, the feed stream contains hydrogen and carbon oxides selected from carbon dioxide or a mixture of carbon dioxide and carbon monoxide and the feed stream comprises at least 10 mol % of $H_2$ based on the total molar content of the feed stream, preferably at least 20 mol %, more preferably at least 30 mol %.

In a preferred embodiment the feed stream contains hydrogen and carbon oxides selected from carbon dioxide or a mixture of carbon dioxide and carbon monoxide and the feed stream comprises at most 90 mol % of $H_2$ based on the total molar content of the feed stream, preferably at most 80 mol %, more preferably at most 70 mol %, even more preferably at most 60 mol %.

In a preferred embodiment, the process is carried out at a reaction temperature of at least 463 K (189.85° C.), preferably of at least 563 K (289.85° C.), more preferably of at least 663 K (389.85° C.).

In another preferred embodiment, the pressure is at least 1 MPa, preferably at least 2 MPa, more preferably at least 3 MPa, even more preferably at least 4 MPa and most preferably at least 5 MPa.

In a preferred embodiment, the weight hourly space velocity (WHSV) is in the range of 1,000 to 100,000 cubic centimeters at standard temperature and pressure (STP) of reactant gases per gram of catalyst charged to the reactor per hour, preferably 2,000 to 50,000 $cm^3_{STP}$ $g_{cat}$ $h^{-1}$, more preferably 5,000 to 40,000 $cm^3_{STP}$ $g_{cat}$ $h^{-1}$, and more preferably 15,000 to 40,000 $cm^3_{STP}$ $g_{cat}$ $h^{-1}$.

In a preferred embodiment the process can be carried out with a stable performance with respect to activity and selectivity during more than 100 h, preferably more than 1,000 h, more preferably more than 10,000 h, and even more preferably more than 100,000 h without the need of reactivation or replacement of the catalyst.

In an embodiment, the process is carried out in a fixed-bed or in a fluidized-bed reactor comprising at least one catalytic bed. Such reactors are well-known from the person skilled in the art and for instance described in EP2257366 or in U.S. Pat. No. 7,279,138.

Test Methods and Definitions

Activity for methanol synthesis reaction is determined using a home-made fixed-bed reactor set-up, which has been described in detail previously (M.S. Frei et al. *J. Catal.*, 2018, 361, 313-321). Briefly, it comprises a high-pressure continuous-flow fixed-bed reactor with an inner diameter of 2.1 mm surrounded by an electric furnace. The reactor was loaded with 100 mg of catalyst with a particle size of 100-125 μm, which was held in place by a bed of quartz wool and was heated from ambient temperature to 553 K (5 K $min^{-1}$) at 5 MPa under a He flow of 20 $cm^3_{STP}$ $g_{cat}$ $min^{-1}$. After 3 h, the gas flow was switched to the reactant mixture (40 $cm^3_{STP}$ $min^{-1}$) comprising $H_2$ and $CO_2$ (Messer, 99.997% and 99.999%, respectively) in a molar ratio of 4:1. A constant flow (2.5 $cm^3_{STP}$ $min^{-1}$) of 20 mol % $CH_4$ in He (Messer, both 99.999%) was added to the effluent stream to serve as an internal standard. The effluent stream was sampled every 12 min and analyzed by an online gas chromatograph (GC, Agilent 7890A), equipped with two parallel columns (Agilent GS Gaspro and Agilent DB-1) connected to a flame ionization detector (FID) and a thermal conductivity detector (TCD), to determine the mol % content of the reactants $H_2$, $CO_2$, and CO in the feed stream and the mol % content of the reactants and the methanol product in the outlet stream.

For each compound i, the response factor $F_i$ respective to the internal standard ($CH_4$) was calculated by the following equation:

$$F_i = \frac{A_i / \dot{n}_i^{in}}{A_{CH_4} / \dot{n}_{CH_4}^{in}}$$

where $A_i$ is the integrated area determined for compound i by the GC and $\dot{n}_i^{in}$ corresponds to its known adjusted molar flowrate. Each response factor was calculated as the average of 5 calibration points around the expected concentration of the respective analyte, i.

Upon reaction the unknown effluent molar flowrate $\dot{n}_i^{out}$ was determined by the following equation:

$$\dot{n}_i^{out} = \frac{A_i \times F_i}{A_{CH_4}} \times \dot{n}_{CH_4}^{in}$$

$CO_2$ conversion ($X_{CO2}$), methanol selectivity ($S_{MeOH}$) and yield ($Y_{MeOH}$) in percent and methanol space-time yield ($STY_{MeOH}$) were calculated applying the following equations:

$$X_{CO_2} = \frac{\dot{n}_{CO_2}^{in} - \dot{n}_{CO_2}^{out}}{\dot{n}_{CO_2}^{in}} \times 100$$

$$S_{MeOH} = \frac{\dot{n}_{MeOH}^{in} - \dot{n}_{MeOH}^{out}}{\dot{n}_{CO_2}^{in} - \dot{n}_{CO_2}^{out}} \times 100$$

$$Y_{MeOH} = X_{CO_2} \times S_{MeOH}$$

$$STY_{MeOH} = \frac{\dot{n}_{MeOH}^{in} - \dot{n}_{MeOH}^{out}}{W_{cat}} \times M_{MeOH}$$

where $W_{cat}$ is the weight of the loaded catalyst and $M_{MeOH}$ is the molar weight of methanol (32.04 g $mol^{-1}$).

Data reported correspond to the average of the 4 measurements preceding a specific time-on-stream, or to the average of 7 measurements collected during each individual condition when temperature or gas flows were altered. The carbon loss in percent was determined for each experiment according to equation 4 and was found to be always less than 3%.

$$\varepsilon_C = \frac{\dot{n}_{CO_2}^{out} - \dot{n}_{MeOH}^{out} - \dot{n}_{CO}^{out}}{\dot{n}_{CO_2}^{in} + \dot{n}_{MeOH}^{in}} \times 100$$

The absence of intra- and extraparticle diffusion limitations was corroborated by the fulfillment of the Weisz-Prater and Carberry criteria.

Powder XRD analysis was performed using a PANalytical X'Pert Pro MPD instrument, utilizing Cu—Kα radiation (λ=0.1541 nm), an angular step size of 0.05° 2θ and a counting time of 12 seconds per step. The average crystal size of $In_2O_3$ was estimated from the (222) reflection applying the Scherrer equation.

XPS analysis was performed in a Physical Electronics Instruments Quantum 2000 spectrometer using monochromatic Al Kα radiation generated from an electron beam operated at 15 kV and 32.3 W. The spectra were collected under ultra-high vacuum conditions (residual pressure=5× $10^{-8}$ Pa) at a pass energy of 46.95 eV. All spectra were referenced to the C 1s peak at 284.8 eV. Although samples were extracted from the reactor in inert atmosphere, the design of the instrument made a brief (<2 min) exposure to air upon sample introduction unavoidable.

STEM-EDX measurements were performed using a Talos F200X instrument operated at 200 kV and equipped with a FEI SuperX detector.

The metal composition of the calcined samples was determined by inductively coupled plasma-optical emission spectrometry (ICP-OES) using a Horiba Ultra 2 instrument equipped with photomultiplier tube detector. Prior to analysis, the catalysts were dissolved in aqua regia and the resulting solutions were diluted with twice-distilled water Specific surface area and pore volume were determined from the sorption isotherm of N2 at 77 K using a Micromeritics TriStar II analyzer. The Brunauer-Emmett-Teller (BET) method was applied for calculating the specific surface area according to ASTM D3663-03 and the volume of gas adsorbed at saturation pressure was used to determine the pore volume.

Temperature-programmed reduction with $H_2$ ($H_2$-TPR) was carried out at the reaction pressure (5.0 MPa) in a Micromeritics AutoChem HP II analyser. 100 mg of catalyst was used for each analysis. A drying step in 100 $cm^3_{STP}$ $min^{-1}$ Argon was carried out at 0.1 MPa between 303-393 K, at a heating rate of 5 K $min^{-1}$ and a hold time of 60 min at the final temperature. Thereafter, the temperature was lowered to 183 K at a rate of 5 K $min^{-1}$ and reduction with 5% $H_2$ in Argon at a flow rate of 50 $cm^3_{STP}$ $min^{-1}$ was carried out between 183-1103 K, with a heating rate of 5 K $min^{-1}$, at a pressure of 5.0 MPa, and a hold time of 30 min at the final temperature.

EXAMPLES

The advantages of the present invention are illustrated in the following examples. However, it is understood that the invention is by no means limited to these specific examples.

Example 1—Catalyst Synthesis

Materials were prepared through a co-precipitation method. Various metals (Pd, Pt, Cu, Ag, Ru, Os) were precipitated with indium to enhance the intermixing among $In_2O_3$ and the noble metal in the working catalyst. The noble metal loading ranged from 0 to 5 wt. % based on the total weight of the calcined catalyst.
Co-Precipitation (CP):
An example of a catalyst containing 0.75 wt. % Pd is as follows: $In(NO_3)_3 \cdot xH_2O$ (3.48 g, Sigma-Aldrich, 99.99%, x=6.9) and $Pd(NO_3)_2 \cdot xH_2O$ (34.8 mg, Sigma-Aldrich, >99.99% metals basis, x=5.5) were dissolved in deionized water (50 $cm^3$) in a round-bottomed flask. In a second vessel, a $Na_2CO_3$ solution was prepared by hydrolyzing $Na_2CO_3$ (10.0 g) in deionized water (100 $cm^3$). 38.8 $cm^3$ of the $Na_2CO_3$ solution were added dropwise (3 $cm^3$ $min^{-1}$) to the solution of metal nitrates under magnetic stirring at ambient temperature to reach a pH value of 9.2. The resulting slurry was aged for 60 min. After adding deionized water (50 $cm^3$), the precipitate was separated by high-pressure filtration, washed with deionized water (3 times, 500 $cm^3$ each time), dried in a vacuum oven (1.5 kPa, 323 K, 1.5 h), and calcined in static air (573 K, 3 h, 2 K $min^{-1}$).
For comparison, materials were also prepared through spray deposition and dry impregnation methods.
Spray Deposition (SD):
Palladium (nominal loading=0.5, 1, and 2 wt. %) was deposited onto $In_2O_3$ by means of spray deposition in a Büchi Mini Spray Dryer B-290. After priming the spray dryer with deionized water, a slurry containing 10 $cm^3$ of deionized water, 1 g of $In_2O_3$, and 0.059, 0.119, or 0.179 g of a palladium nitrate solution (8.5 wt. % Pd in diluted nitric acid, ABCR-Chemicals) was fed to the dryer. The following parameters were set on the instrument: aspiration=80% (ca. 28 $m^3$ $h^{-1}$), spray gas (air) flow=0.6 $m^3$ $h^{-1}$ at 0.6 MPa, pump=10% (ca. 1 $cm^3$ $min^{-1}$), inlet temperature=593 K, and nozzle cleaner=0. The sample was unloaded from the collector and calcined for 3 h at 373 K (2 K $min^{-1}$) in static air.
Dry Impregnation (DI):
A 25-$cm^3$ round-bottomed flask was loaded with $Pd(NO_3)_2 \cdot xH_2O$ (23.5 mg) and deionized water (0.39 g). $In_2O_3$ (1.00 g) and 5 stainless steel spheres (radius=3 mm) were added and the flask was rotated (ca. 45 rpm) using a Büchi R-114 rotation evaporator at ambient temperature and pressure. After 12 h, the pressure was lowered to 2 kPa and the temperature raised to 333 K for 1 h to allow the evaporation of the solvent. The thus obtained samples were calcined for 3 h at 373 K (2 K $min^{-1}$) in static air.

Figure 2:
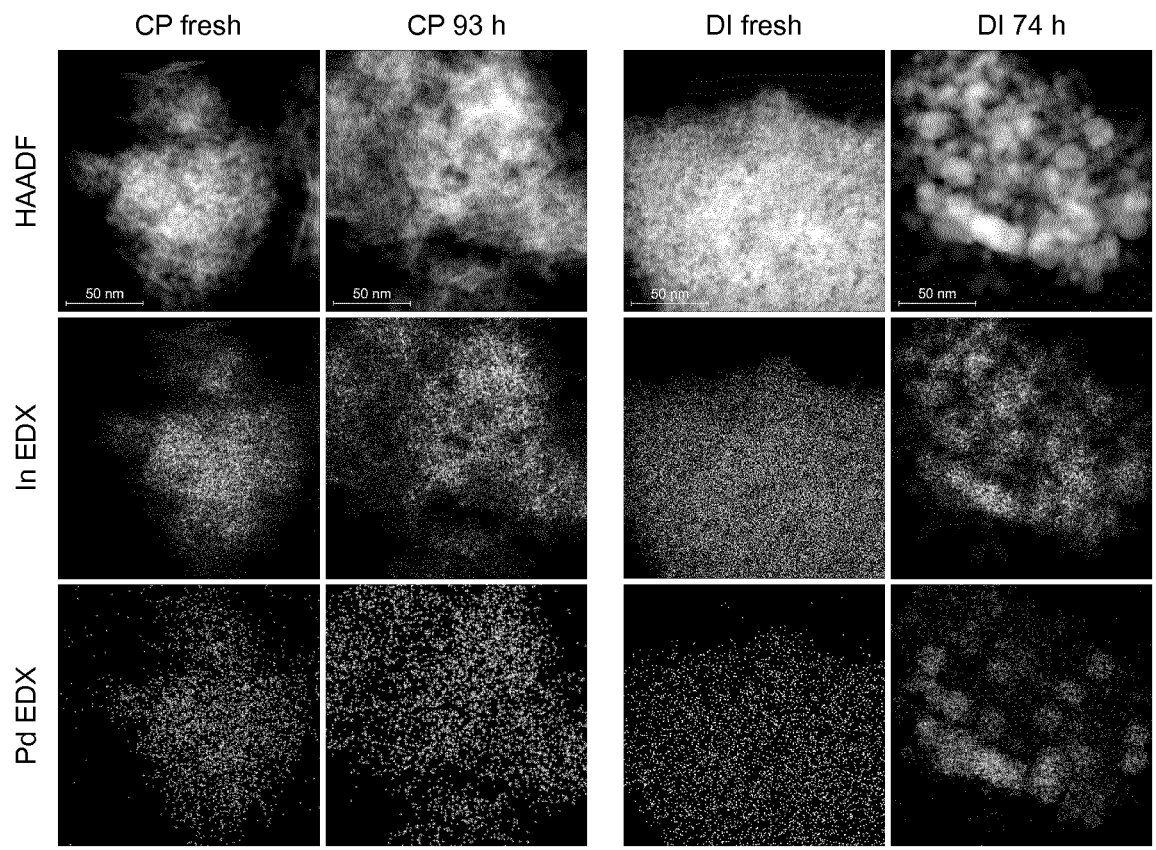
FIG. 2 shows the results of the analysis by scanning transmission electron microscopy coupled to energy-dispersive X-ray spectroscopy (STEM-EDX) of Pd—$In_2O_3$ samples prepared by dry impregnation and co-precipitation in fresh form and after use in the reaction.
Figure 3:
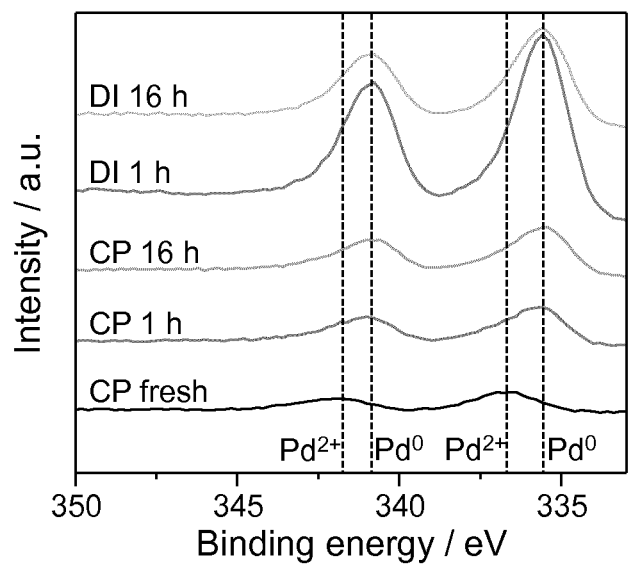
FIG. 3 shows the X-ray photoelectron (XPS) spectra of the materials prepared by co-precipitation and dry impregnation in fresh form and after use for 16 h in the reaction.
Figure 4:
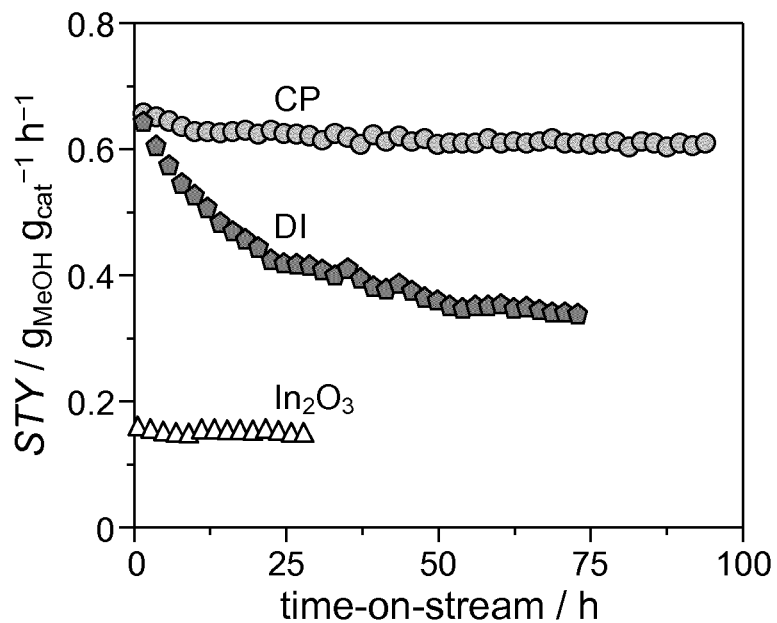
FIG. 4 shows the evolution of the space-time yield of methanol over time-on-stream for the materials prepared by co-precipitation and dry impregnation.
Figure 5:
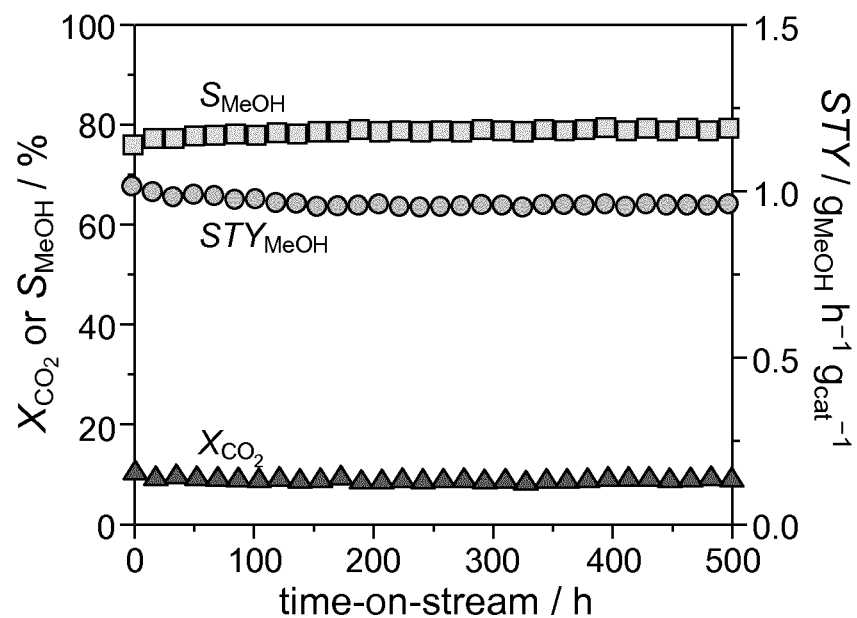
FIG. 5 is an extended stability test under optimized reaction conditions of the catalyst prepared by co-precipitation.

Characterization data of the products are provided in Table 1 and FIGS. 1-3. FIG. 1: XRD of DI and CP samples of indium oxide with 0.75 wt. % Pd. Fresh catalysts are indistinguishable using XRD due to the overlap of peaks of the respective components and the small size of the Pd particles. The used materials correspond to the catalysts extracted from the reactor after the tests depicted in FIG. 4. The DI sample produced a reflection specific to Pd, which is absent for the used CP material.

FIG. 2: STEM-EDX of the same samples as in FIG. 1 evidencing very high dispersion of the noble metal in both materials prior to use in the reaction. However, the used CP sample appears unaltered, while severe sintering (i.e., increase of particle size) is observed for the oxide as well as the noble metal phase in the DI material.

FIG. 3: XPS Pd 3d core-level spectra of the CP and DI catalysts prior to and after use for 16 h in the reaction. Prior to the reaction, the CP material features oxidic Pd species which are quickly reduced to $Pd^0$ upon exposure to the reaction environment. After this initial activation, the Pd 3d signal remains unaltered in shape and intensity for further 15 h on stream, as expected based on the observed stability of this material. Pd is almost three times more abundant on the surface of the catalyst prepared by DI (1.1 at. %) as compared to the CP sample (0.4 at. %). Since both materials possess the same bulk metal loading (0.75 wt. %), it is deduced that a significant quantity of Pd is incorporated in the bulk of the oxide crystals in this solid.

Example 2—Catalyst Testing

The reactor was loaded with 50 mg of catalyst with a crystal size of 100-125 μm, which was diluted in 50 mg of $TiO_2$ (100-125 μm, Sigma-Aldrich, >99.9%) and held in place by a bed of quartz wool and heated from ambient temperature to 553 K (5 K $min^{-1}$) at 0.5 MPa under a He flow of 20 $cm^3_{STP}$ $min^{-1}$. After 3 h at 553 K, the pressure was raised to 5 MPa in the same stream, which typically took 20 min. Then, the gas flow was switched to the reactant mixture (40 $cm^3_{STP}$ $min^{-1}$) corresponding to a weight hourly space velocity (WHSV) of 48,000 $h^{-1}$, with a $H_2$:$CO_2$ ratio of 4. The effluent stream was sampled after 1 h on stream and then every 12 min and at least 7 measurements were averaged under each set of reaction conditions. 2.5 $cm^3_{STP}$ $min^{-1}$ of a 20 mol % $CH_4$ in He was used as an internal standard by injecting a constant flow after the reactor outlet. Tests were carried out up to 500 h time-on-stream). The results are provided in Table 2 and in FIG. 4.

The presence of any noble metal produced an increase in productivity. However, the choice of said metal is important. The productivity is increased to a much more significant extent only when Pt or Pd are employed. Concerning Pd-promoted catalysts, only materials prepared by the CP technique retained their performance, while materials prepared by deposition or impregnation methods rapidly deactivated (see Table 2).

TABLE 1

Characterization data of selected catalysts. Samples discussed in FIG. 1-5 are marked in bold.

| Support | Promoter | Nominal promoter loading [wt. %] | Synthesis | $V_{pore}$ [cm$^3$ g$^{-1}$] | $S_{BET}$ [m$^2$ g$^{-1}$] | ICP-OES promoter loading [wt. %] |
|---|---|---|---|---|---|---|
| $In_2O_3$ | — | — | — | 0.37 | 125 | — |
| $In_2O_3$ | Pd | 0.25 | CP | 0.40 | 147 | 0.31 |
| $In_2O_3$ | Pd | 0.75 | CP | 0.51 | 174 | 0.74 |
| $In_2O_3$ | Pd | 1.5 | CP | 0.56 | 149 | 1.45 |
| $In_2O_3$ | Pd | 3.5 | CP | 0.53 | 158 | 3.36 |
| $In_2O_3$ | Pd | 0.25 | DI | 0.36 | 127 | 0.25 |
| $In_2O_3$ | Pd | 0.75 | DI | 0.35 | 131 | 0.73 |
| $In_2O_3$ | Pd | 3.5 | DI | 0.26 | 113 | 3.43 |
| $In_2O_3$ | Pd | 0.75 | SD | 0.40 | 131 | 0.63 |
| $ZrO_2$ | — | — | — | 0.45 | 110 | — |
| $ZrO_2$ | Pd | 0.75 | DI | 0.32 | 102 | 0.73 |
| $ZrO_2$ | Pd | 0.75 | CP | 0.50 | 195 | 0.69 |
| $TiO_2$ | — | — | — | 0.15 | 59 | — |
| $TiO_2$ | Pd | 0.75 | DI | 0.12 | 58 | 0.72 |
| $TiO_2$ | Pd | 0.75 | CP | 0.09 | 24 | 0.68 |
| $In_2O_3$ | Ag | 0.75 | CP | 0.40 | 146 | 0.71 |
| $In_2O_3$ | Ru | 0.75 | CP | 0.38 | 134 | 0.78 |
| $In_2O_3$ | Cu | 0.75 | CP | 0.43 | 157 | 0.75 |
| $In_2O_3$ | Pt | 0.75 | CP | 0.44 | 150 | 0.74 |

TABLE 2

Catalytic performance in the direct hydrogenation of $CO_2$ to methanol of selected catalysts. Samples discussed in FIG. 1-5 are marked in bold. Conditions applied in all tests: 553 K, 5 MPa, molar $H_2:CO_2$ = 4.

| Support | Promoter | Synthesis | ICP-OES Promoter loading [wt. %] | WHSV [cm$^3_{STP}$ g$_{cat}$ h$^{-1}$] | $X_{CO2}$ [%] | $S_{MeOH}$ [%] | Initial $STY_{MeOH}$ (and after 16 h) [g$_{MeOH}$ g$_{cat}^{-1}$ h$^{-1}$] |
|---|---|---|---|---|---|---|---|
| $In_2O_3$ | — | — | — | 24,000 | 2.3 | 90 | 0.16 (0.15) |
| $In_2O_3$ | Pd | CP | 0.31 | 24,000 | 8.2 | 85 | 0.48 (0.47) |
| $In_2O_3$ | Pd | CP | 0.74 | 24,000 | 11.5 | 78 | 0.66 (0.61) |
| $In_2O_3$ | Pd | CP | 0.74 | 48,000 | 9.7 | 75 | 1.01 (1.00) |
| $In_2O_3$ | Pd | CP | 1.45 | 24,000 | 12.3 | 72 | 0.64 (0.61) |
| $In_2O_3$ | Pd | CP | 3.36 | 24,000 | 5.4 | 89 | 0.33 (0.29) |
| $In_2O_3$ | Pd | DI | 0.25 | 24,000 | 2.2 | 78 | 0.18 (0.15) |
| $In_2O_3$ | Pd | DI | 0.73 | 24,000 | 9.6 | 76 | 0.64 (0.43) |
| $In_2O_3$ | Pd | DI | 3.43 | 24,000 | 10.1 | 74 | 0.63 (0.33) |
| $In_2O_3$ | Pd | SD | 0.63 | 24,000 | 9.8 | 78 | 0.61 (0.39) |
| $ZrO_2$ | — | — | — | 24,000 | 0 | — | 0 (0) |
| $ZrO_2$ | Pd | DI | 0.73 | 24,000 | 7.3 | 29 | 0.15 (0.13) |
| $ZrO_2$ | Pd | CP | 0.69 | 24,000 | 2.1 | 10 | 0.02 (0.02) |
| $TiO_2$ | — | — | — | 24,000 | 0 | — | 0 (0) |
| $TiO_2$ | Pd | DI | 0.72 | 24,000 | 7.2 | 7 | 0.01 (0) |
| $TiO_2$ | Pd | CP | 0.68 | 24,000 | 0.9 | 5 | 0.01 (0.01) |
| $In_2O_3$ | Ag | CP | 0.71 | 24,000 | 3.3 | 82 | 0.18 (0.17) |
| $In_2O_3$ | Ru | CP | 0.78 | 24,000 | 4.0 | 84 | 0.23 (0.22) |
| $In_2O_3$ | Cu | CP | 0.75 | 24,000 | 3.1 | 32 | 0.18 (0.17) |
| $In_2O_3$ | Pt | CP | 0.74 | 24,000 | 4.4 | 89 | 0.27 (0.25) |

Example 3—Catalyst Differentiation

Figure 6:
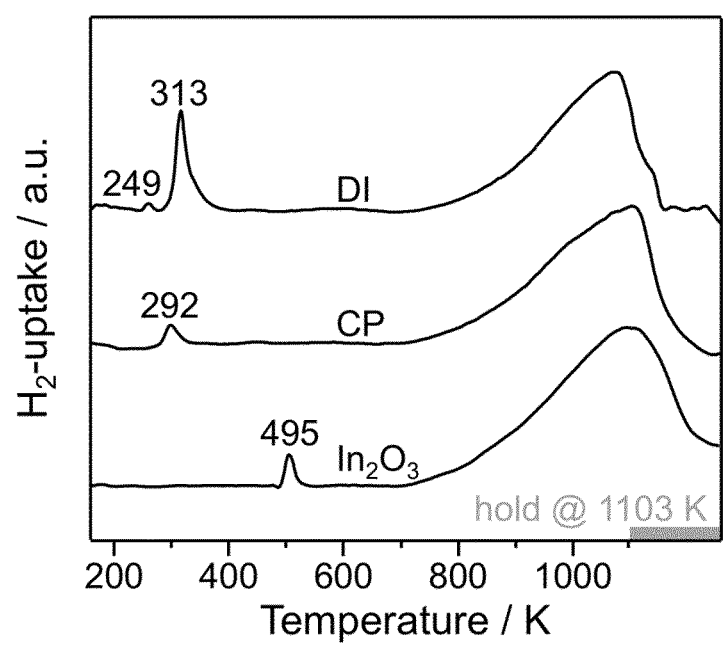
FIG. 6 depict the temperature-programmed reduction with hydrogen ($H_2$-TPD) analysis that was performed at 5.0 MPa.

Two samples of catalysts have been prepared, one by co-precipitation (CP) and the other one by deposition impregnation (DI). $H_2$-TPD was performed at 5.0 MPa (FIG. 6) resulting in a temperature of around 313 K for the material prepared by DI versus 293 K for the material prepared by CP.

The invention claimed is:

1. A Method to prepare a catalyst for use in a process for the synthesis of methanol, comprising indium oxide in the form of $In_2O_3$, and at least one additional metal selected from a noble metal; and in that the average particle size of said noble metal phase is, at least 0.05 nm, and less than 5 nm as determined by STEM-EDX, characterized in that the catalyst is prepared by co-precipitation of a saline solution at a pH above 8.5 comprising an indium salt and a salt of the at least one additional metal selected from a noble metal and optionally further comprising a salt of the at least one alkaline earth metal; comprising a further calcination step of the catalyst, wherein the calcined catalyst obtained comprised from 0.01 to 1.0 wt. % of the additional noble metal based on the total weight of the calcined catalyst and wherein the catalyst content of indium oxide in the form of $In_2O_3$ based on the calcined catalyst is ranging from 60 to 99.99 wt. %.

2. The method according to claim 1, characterized in that the co-precipitation is performed at a pH above 9; and at a temperature of at least 293 K (19.85° C.).

3. The method according to claim 1, characterized in that the catalyst is a calcined catalyst, and in that the method comprises a step of calcination of the catalyst performed at a temperature of at least 473 K (199.85° C.).

4. The method according to claim 1, characterized in that said catalyst further comprises at least one alkaline earth metal.

5. The method according to claim 1, characterized in that said catalyst further comprises at least one alkaline earth metal being incorporated simultaneously with said indium salt and a said salt of the at least one additional metal selected from a noble metal at the co-precipitation stage.

6. The method according to claim 1 characterized in that said $In_2O_3$ is present in the form of particles having an average crystal size of less than 20 nm as determined by XRD.

7. The method according to claim 1 characterized in that said $In_2O_3$ is present in the form of particles having an average crystal size of less than 10 nm as determined by XRD.

8. The method according to claim 1, characterized in that said at least one additional metal is a noble metal selected from ruthenium (Ru), rhodium (Rh), palladium (Pd), silver (Ag), osmium (Os), platinum (Pt), copper (Cu), gold (Au), iridium (Ir), and any combination thereof.

9. The method according to claim 1, characterized in that said at least one additional metal is a noble metal selected palladium (Pd) and/or platinum (Pt).

10. The method according to claim 1, characterized in that the average particle size of the noble metal phase obtained on said catalyst is less than 4 nm as determined by STEM-EDX.

11. The method according to claim 1, characterized in that the average particle size of the noble metal phase obtained on said catalyst is less than 2 nm as determined by STEM-EDX.

* * * * *